United States Patent [19]
Vinson

[11] Patent Number: 6,011,015
[45] Date of Patent: *Jan. 4, 2000

[54] ANGIOTENSIN II FOR IMPROVING FERTILIZATION

[75] Inventor: Gavin Paul Vinson, London, United Kingdom

[73] Assignee: Queen Mary & Westfield College, London, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/750,316

[22] PCT Filed: May 25, 1995

[86] PCT No.: PCT/GB95/01202

§ 371 Date: Nov. 22, 1996

§ 102(e) Date: Nov. 22, 1996

[87] PCT Pub. No.: WO95/32725

PCT Pub. Date: Dec. 7, 1995

[30] Foreign Application Priority Data

May 27, 1994 [GB] United Kingdom .................. 9410639

[51] Int. Cl.$^7$ .................................................. A61K 38/00
[52] U.S. Cl. ............................................. 514/16; 530/316
[58] Field of Search ............................. 530/316; 514/12, 514/16

[56] References Cited

U.S. PATENT DOCUMENTS 5,338,744  8/1994  Dudley et al. ........................ 514/303

OTHER PUBLICATIONS

C. De Geyter, et al.; Int. Journal of Andrology, 15, pp. 485–497 (1992).

H. Holland–Moritz and W. Krause; Int. Journal of Andrology, 15, pp. 473–485 (1992).

G.J. Vulcano, et al.; Mathematical Biosciences, 149, pp. 77–93 (1998).

S.T. Mortimer and D. Mortimer, Journal of Andrology, 11, pp. 195–203 (1990).

S.T. Mortimer, Human Reproduction Update, 3 (5), pp. 403–439 (1997).

Koyama Norihiro, *Kyorin Igakkai Zasshi*, vol. 24, No. 4, pp. 517–528, 1993.

Sharpe et al., *J. Physiol.* (London), 239(3), pp. 595–622, 1974.

Koyama Norihiro, *Kyorin Igakkai Zasshi*, vol. 24, No. 4, pp. 517–528 (abstract), 1993.

Mizutani et al., *Andrologia* 17(2): 150–156, 1985.

Kaneko et al., *J. Pharm. Dyn.* 7, pp. 87–93, 1984.

*Primary Examiner*—Michael P. Woodward
*Assistant Examiner*—C. Delacroix-Muirheid
*Attorney, Agent, or Firm*—Fay, Sharpe, Fagan, Minnich & McKee, LLP

[57] ABSTRACT

Angiotensin II, or an analog thereof, can be used for promoting the fertilization of mammalian eggs. A method is disclosed for promoting in vitro fertilization of mammalian eggs using angiotensin II or a salt or an analogue thereof.

21 Claims, 8 Drawing Sheets

FIG. 1(a) UNSTIMULATED CONTROLS

FIG. 1(b) ANGIOTENSIN II STIMULATED, 1 nmol

ANGIOTENSIN II FOR IMPROVING FERTILIZATION

BACKGROUND OF THE INVENTION

The present invention relates to the use of angiotensin II, or an analogue thereof, for promoting fertilization of mammalian eggs, especially human eggs. In particular, it relates to the use of angiotensin II to improve sperm motility. The invention also relates to a method of promoting in vitro fertilization.

Angiotensin II is an octapeptide, usually regarded as being produced in the blood, firstly by the action of renin, an enzyme secreted by the kidney, on angiotensinogen, resulting in the formation of the decapeptide precursor, angiotensin I, and secondly the action of a dipeptidase "angiotensin converting enzyme"; this enzyme acts on angiotensin I to form angiotensin II. Angiotensin II, in turn, undergoes hydrolysis by an aminopeptidase to yield the heptapeptide angiotensin III (angiotensin 1-7).

The hormone angiotensin II (Ang II) forms part of the renin—angiotensin system which helps to control electrolyte balance and blood pressure within the body. There are several tissues within the body upon which Ang II acts, they include the adrenal gland, uterus, liver, brain and kidney.

Amongst the several established functions of angiotensin II, it is known to be involved in vasoconstriction, which leads to hypertension. Most treatments for high blood pressure will include blockage of angiotensin function in one way or another. Ang II also stimulates the secretion of aldosterone by the adrenal cortex. Aldosterone is a potent hormone which acts primarily on the kidney to promote sodium retention and thus inter alia, heightens the hypertensive effects of angiotensin acting directly on the vasculature.

Ang II is known to act on various sites in the brain, and one of its actions in animals is the regulation of thirst and drinking.

Angiotensin also has trophic effects on the vasculature, promoting growth of the muscles in the arterial wall. It is also thought to be angiogenic, i.e. it causes vascularisation of newly developing tissue.

Most of the established effects of Ang II have been found to occur via the $AT_1$ subtype of the Ang II receptor, which is a seven transmembrane domain receptor. This receptor has been cloned and sequenced from a variety of tissues, and has been found to be a 359 amino acid polypeptide with a predicted molecular weight of around 40 kD (Bernstein and Alexander, (1992), *Endocr. Rev.* 13, 381–386). Studies using photo-affinity labeling and cross linking agents have suggested molecular weights for mature receptor of approximately 65 kD and 116 kD, respectively, which may reflect glycosylation of asparagine residues within the extracellular domain.

From the recent development of a hybridoma cell line. see Baker, S., et al, *J. Mol. Endocr.* 11, 241–245, (1993), it has been found possible to produce monoclonal antibodies to the $AT_1$ subtype of the Ang II receptor. In consequence, such receptors have been found to exist both on maturing rat and human sperm tails, and on free swimming sperm obtained by vaginal lavage from mated rats, and in human ejaculated sperm.

SUMMARY OF THE INVENTION

It has now been found that angiotensin II, or an analogue thereof, increases both the percentage of motile sperm and their linear velocity.

This newly discovered property of angiotensin II enable Ang II to be used to promote fertilization, since the capacity of sperm to fertilize ova is closely related to their motility.

According to one aspect of the invention there is provided the use of angiotensin II or a salt or analogue thereof to promote fertilization of mammalian eggs. Such fertilization may take place in vitro.

According to a second aspect of the invention there is provided the use of angiotensin II, or a salt or analogue thereof to increase sperm motility.

According to another aspect of the invention there is provided the use of angiotensin II, or a salt or analogue thereof, for the manufacture of a medicament for use in promoting fertilization, in particular in vitro fertilization.

According to yet another aspect of the invention there is provided a method of promoting in vitro fertilization of mammalian eggs comprising adding angiotensin II or a salt or analogue thereof to incubation medium containing oocytes and sperm.

BRIEF DESCRIPTION OF THE DRAWINGS

FIG. 3 illustrates the effect of angiotensin II and angiotensin II with a monoclonal antibody to the $AT_1$ receptor upon sperm velocity, FIG. 3(a) and sperm motility, FIG. 3(b).

FIG. 6(a and b) illustrates the effect on curvilinear velocity (VEL) for the samples of FIG. 5.

FIG. 7(a and b) illustrates the effect an amplitude of lateral head displacement (ALH) for the samples of FIG. 5.

DESCRIPTION OF THE PREFERRED EMBODIMENT

Standard procedure for in vitro fertilization are described in "In vitro fertilization: a treatment for male infertility:, Cohen, J., Edwards, R. et al, 1985, *Fertility and Sterility*, 44, 422–432. In general, sperm samples are washed in MEM tissue culture medium, centrifuged at approximately 400 g, resuspended and recentrifuged. They are then resuspended in a few drops of MEM and 0.5 ml of fresh medium is layered on top. After 30 min in the incubator at 37° C., the top 30% of the medium, containing essentially motile sperm, is removed and distributed to oocytes (approximately 10,000 sperm per oocyte) in MEM and left for 24 hrs for fertilization to occur.

Angiotensin II, or an analogue thereof, may be added either in the washing stages, or during the final incubation with the oocyte. When added to the incubation medium, angiotensin II, or an analogue thereof, is added at a concentration of preferably 1 nmole/l.

Analogues of angiotensin II which may be used for increasing sperm motility, and thereby promoting fertilization, include angiotensin II amide.

The invention will be further described with reference to the following examples:

EXAMPLE 1
Effect of Angiotensin II Stimulation on Sperm Motility

Human sperm sample were obtained from 12 volunteers and patients attending the Newham Hospital assisted fertility clinic. Samples were suspended in modified minimum essential medium with Earle's salts (MEM) and glutamine and viewed in a Makler chamber using an Olympus inverted microscope fitted with an Olympus ARTF-2 video camera. Fields were recorded on video tape and percentage motility evaluated at 1 min and 5 min. After mixing with MEM alone (unstimulated controls) or with MEM containing 1 nmole/litre angiotensin II amide.

Percentage motility was estimated on playback of the video tapes by freezing the frame to count all of the sperm within a field and then, in forward mode, by counting immotile sperm, i.e. those which within the period of observation did not move to an adjacent square (100 $\mu$meter) on the Makler Chamber grid. In practice, rigid use of this definition was rarely necessary as sperm were either completely immotile or progressed freely.

Figure 1A:
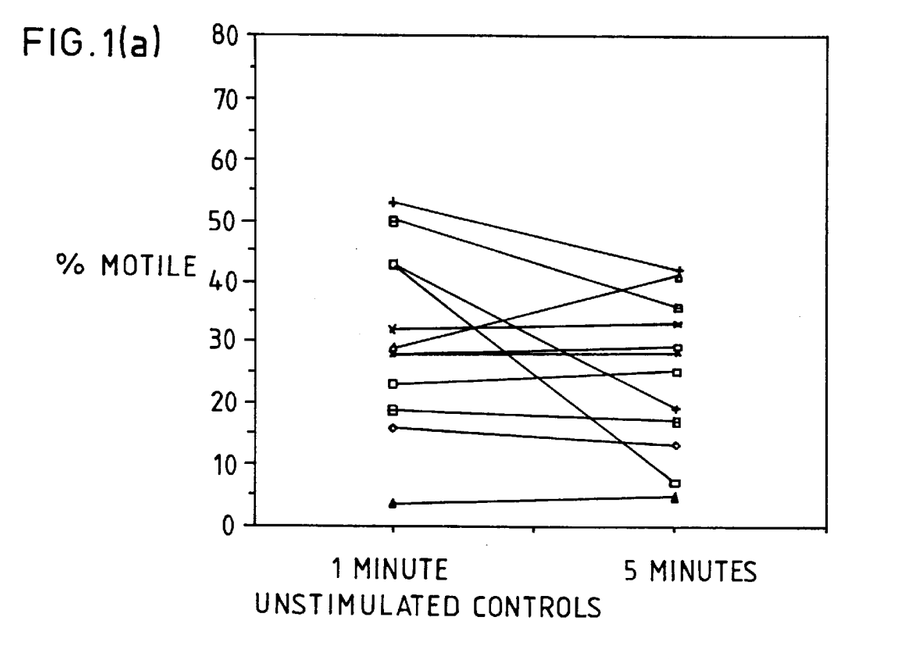
FIG. 1(a) illustrates the percentage motility of unstimulated sperm after 1 and 5 minutes.
Figure 1B:
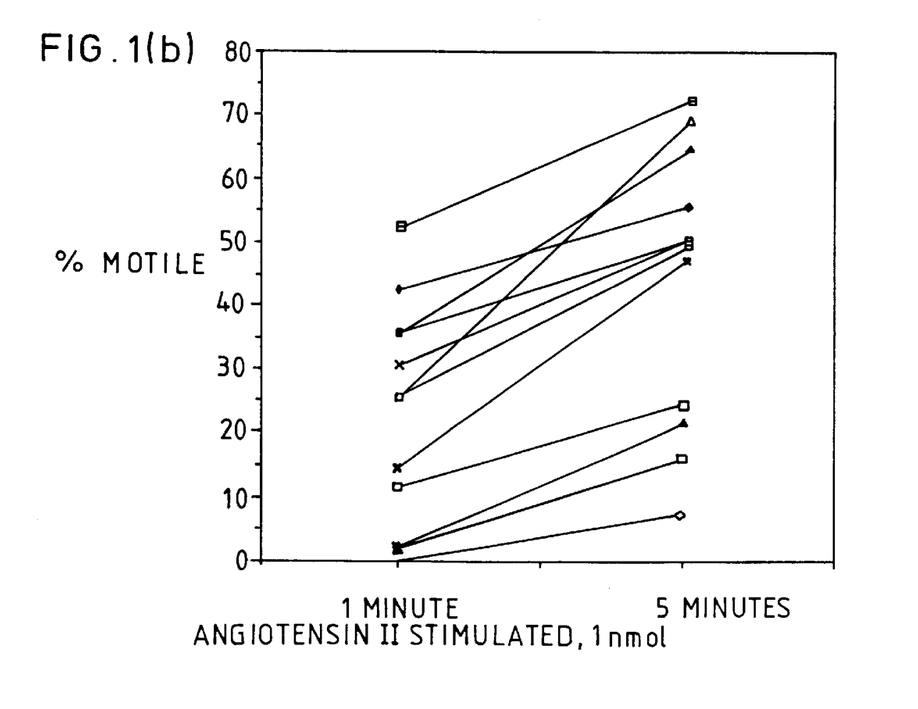
FIG. 1(b) illustrates the percentage motility of sperm stimulated with angiotensin II after 1 and 5 minutes.

From FIG. 1($a$) it can be seen that there was no significant difference in percentage motility after 5 minutes in the unstimulated controls. Within the angiotensin II stimulated group, however, percentage motility after 5 minutes was significantly different from percentage motility after 1 minute.

EXAMPLE 2
Effect of $AT_1$ Receptor Antagonist on Sperm Motility

A series of six sperm samples, obtained from the same source as Example 1, were mixed either with unmodified MEM, or MEM containing DuP-753 (1 nmole/l).

Percentage motility was estimated in the same way as in Example 1.

Figure 2:
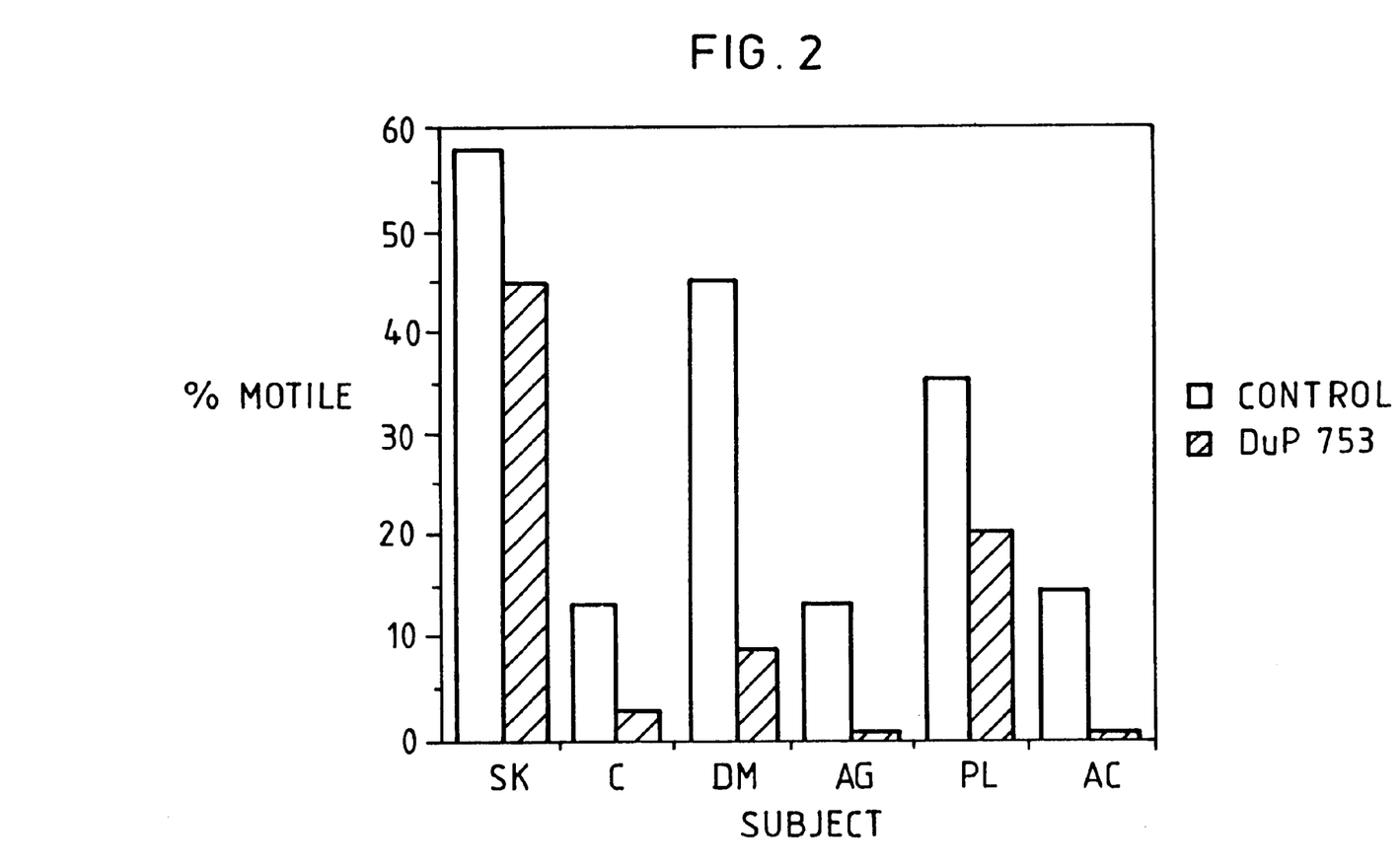
FIG. 2 illustrates the effect of DuP-753 on the percentage motility of sperm.

From FIG. 2 it is evident that, in the presence of DuP-753, (2-n-butyl-4-chloro-5-hydroxymethyl-1-[(2'-(1H-tetrazol-5-yl) biphenyl-4-yl) methyl] imidazole, potassium salt), percentage motility was significantly decreased relative to the untreated controls.

EXAMPLE 3
Effect of Angiotensin II on Sperm Velocity

Sperm samples were obtained from the same source as Example 1. One series of samples was kept as controls. To a second series Angiotensin II amide (10 nmole/l) was added. A third series was treated with monoclonal antibody to the $AT_1$, receptor before angiotensin was added.

Velocity was measured by timing forwardly progressive sperm traversing the grid on the Makler Chamber and timing them manually.

Figure 3A:
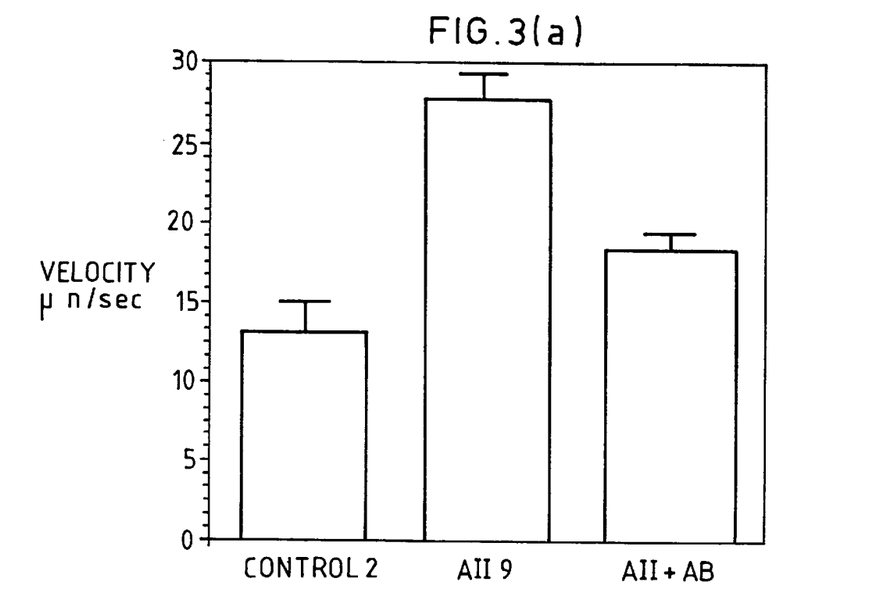

From FIG. 3($a$) it can be seen that stimulation with angiotensin II significantly stimulated forward progressive velocity compared with the untreated controls, whilst addition of the monoclonal antibody inhibited the response to angiotensin II.

Figure 3B:
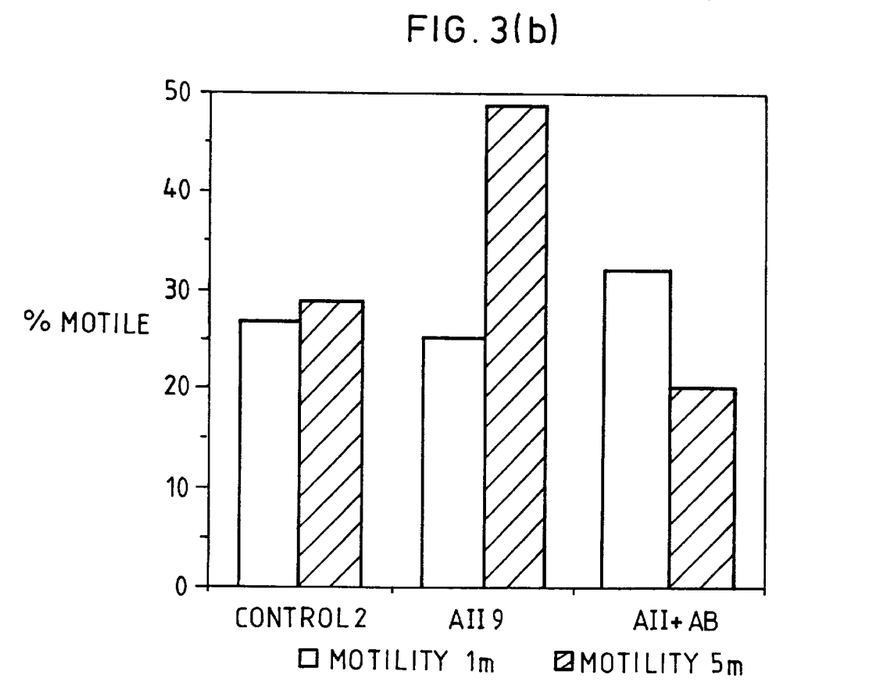

From FIG. 3($b$) it can be seen that similar results were obtained for the effect on the percentage of motile sperm.

EXAMPLE 4

Sperm samples were obtained from the same source as Example 1. One series of samples was kept as controls. A second series was exposed to angiotensin II (1 $\mu$mole/l) for five minutes. A third series was exposed to angiotensin II (1 $\mu$mole/l) for 5 minutes and then DuP-753 (1 $\mu$mole/l) was added.

The percentage of motile sperm was measured using the same method as was used in Example 1.

Figure 4:
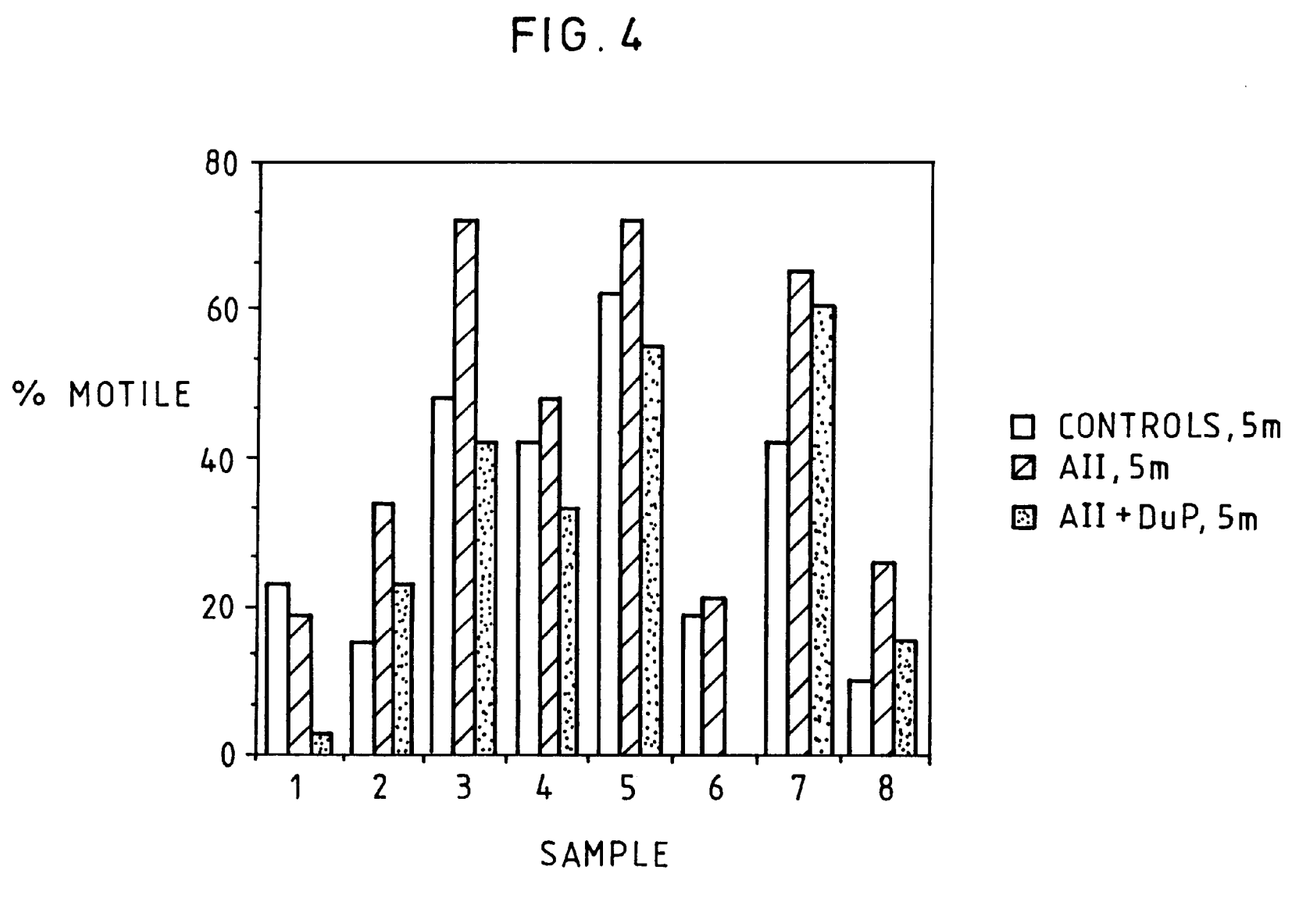
FIG. 4 illustrates the effect of angiotensin II and DuP-753 on sperm motility after 5 minutes.

From FIG. 4 it can be seen that, when compared with the controls, in most samples angiotensin II enhanced the percentage of sperm which were motile after 5 minutes. This enhancement was generally reduced in the samples to which DuP-753 had been added.

EXAMPLE 5
Effect of Angiotensin of Sperm Motility

Sperm samples were obtained from the same source as Example 1. One series of samples was kept as controls. TO a second series angiotensin II amide (1 nmole/l) was added.

Sperm motility was assayed by using a computer system which measures different aspects of sperm motility, namely curvilinear velocity (VCL) and amplitude of lateral head displacement (ALH).

Figure 5A:
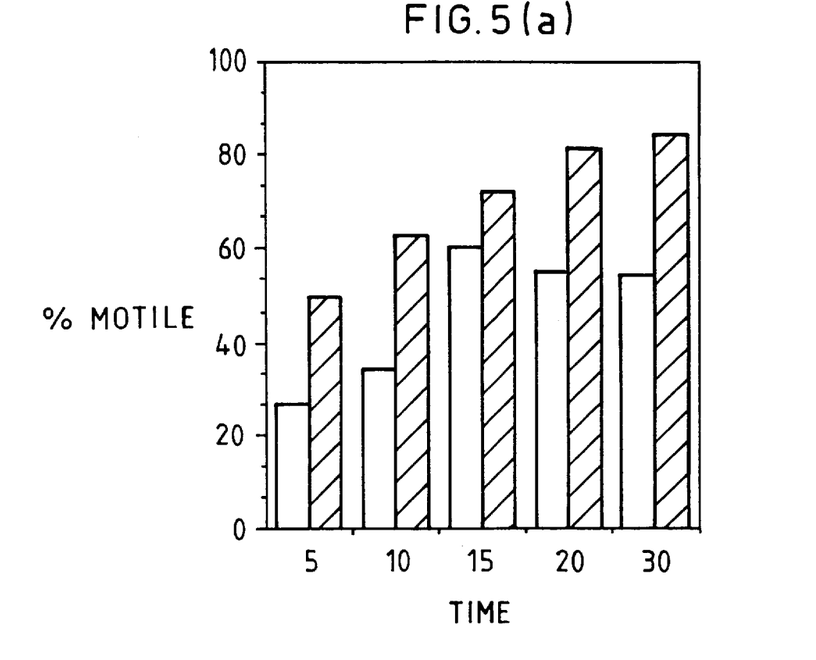
FIGS. 5(a) and 5(b) illustrates the effect of angiotensin II amide on sperm motility for two samples over a 30 minute period.
Figure 5B:
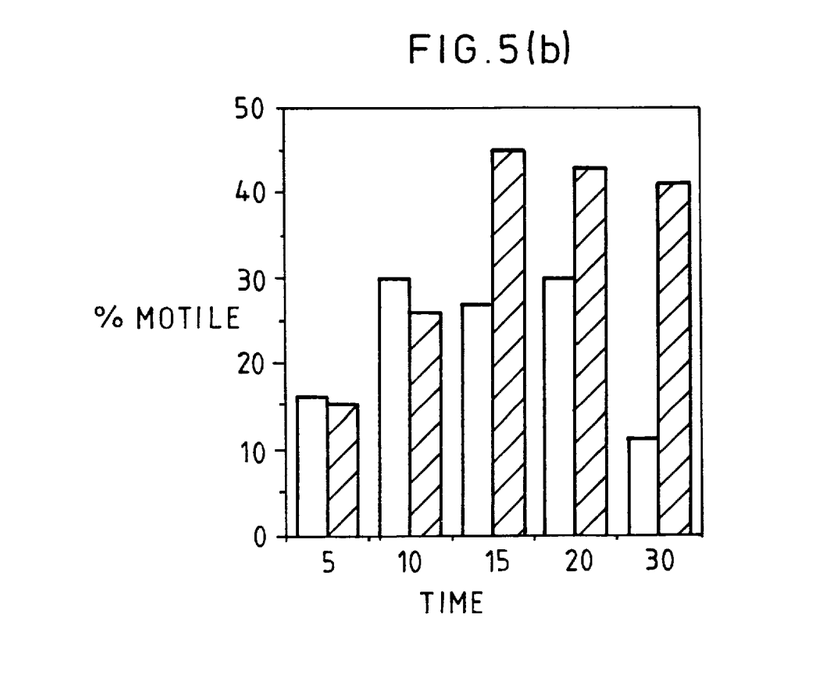

FIGS. 5($a$) and 5($b$) show the percentage of motile sperm in each of two samples, over a 30 minute period in the presence (shaded bars) and absence (clear bars) of angiotensin II amide (1 nmole/l).

Figure 6A:
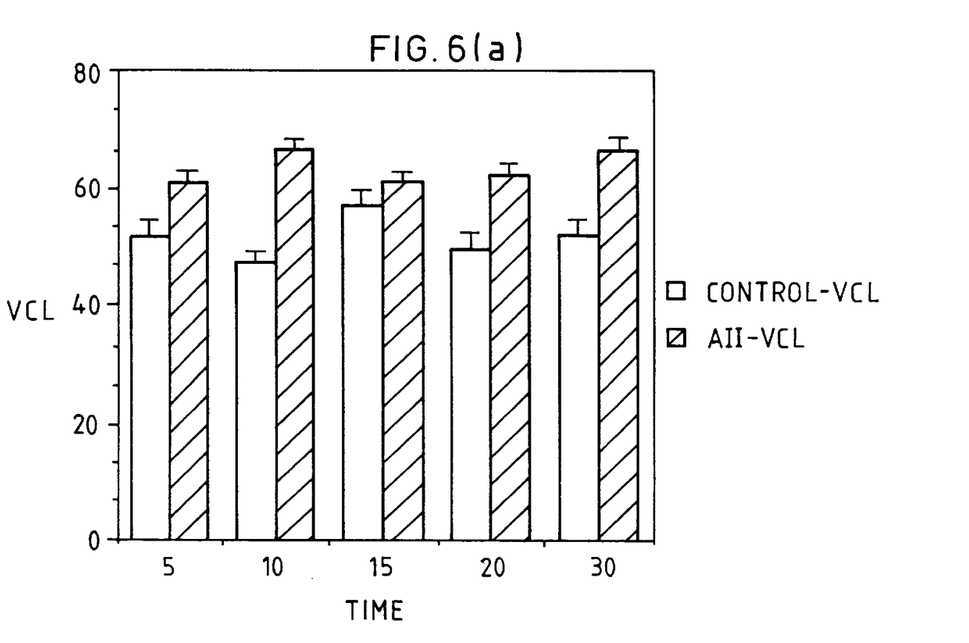
Figure 6B:
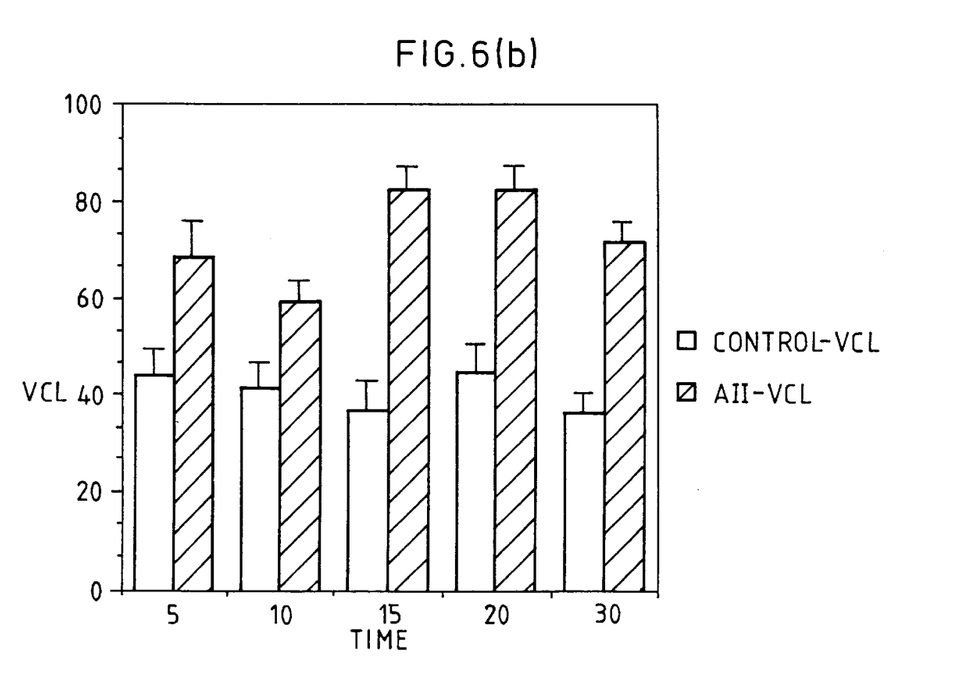

FIGS. 6($a$) and 6($b$) show the same samples assayed for VCL.

Figure 7A:
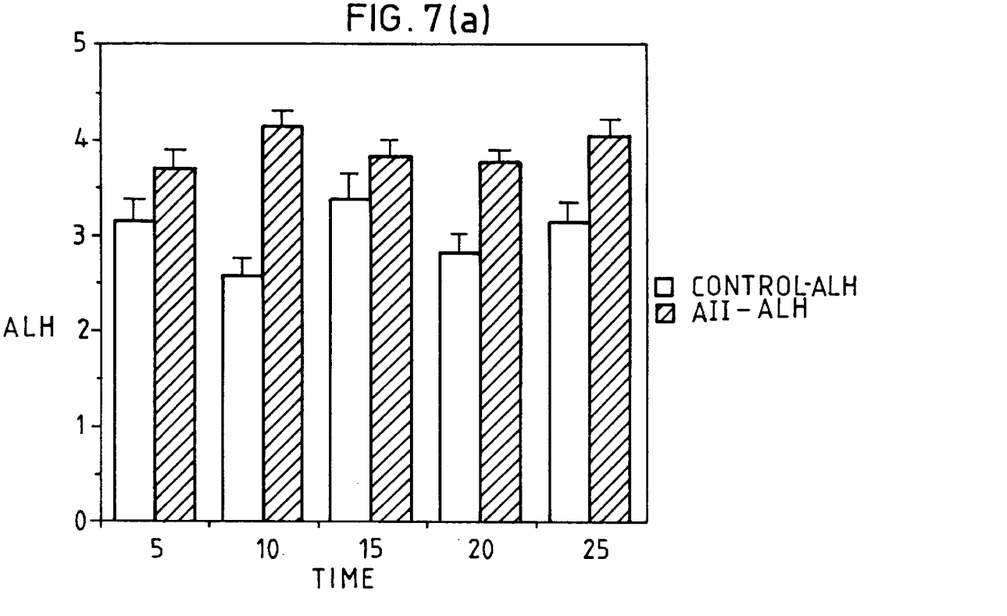
Figure 7B:
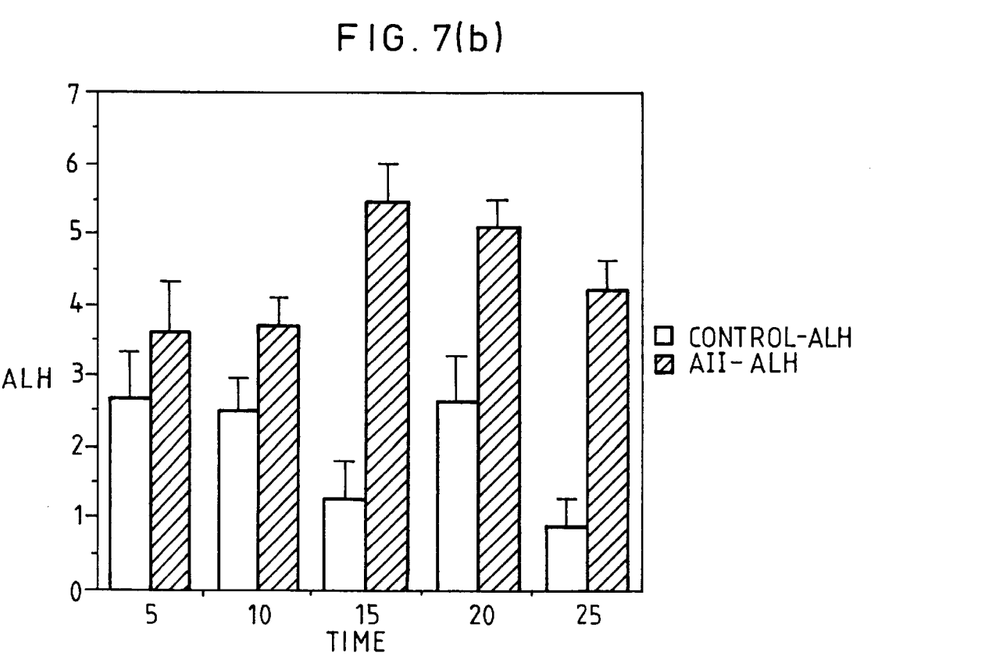

FIGS. 7($a$) and 7($b$) show the same samples assayed for ALH.

Figure 8:
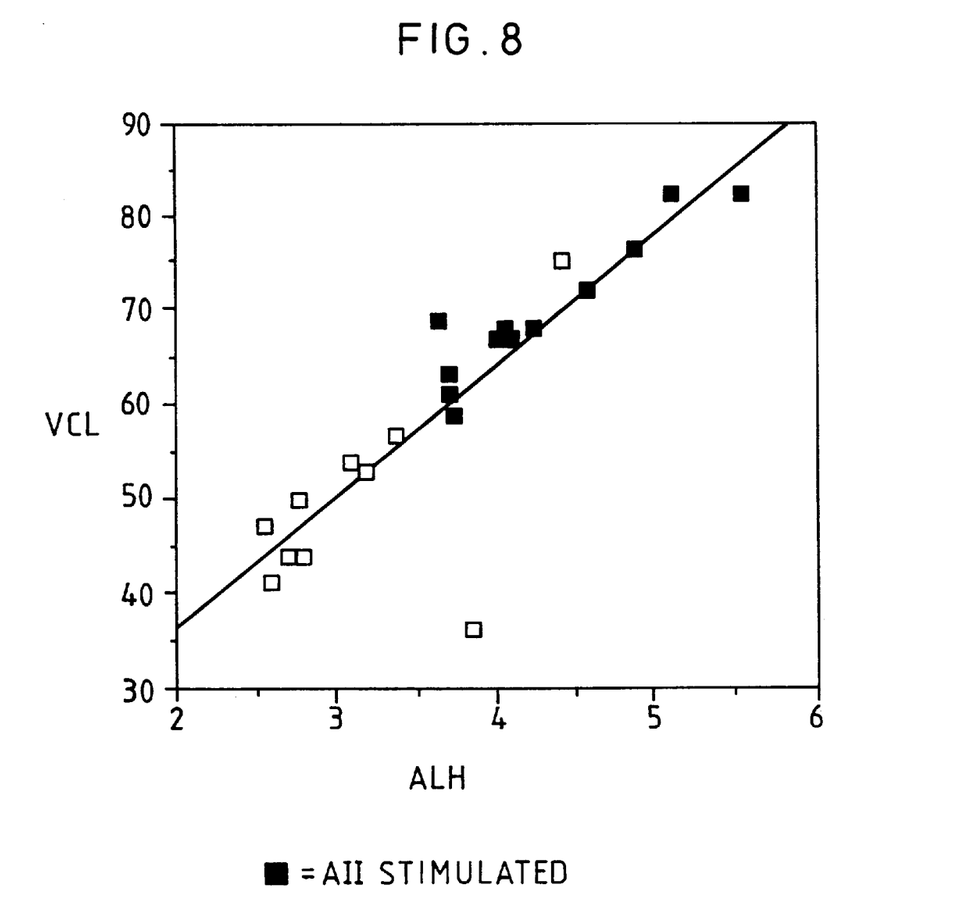
FIG. 8 illustrates the effects of angiotensin II (solid symbols) on VCL and ALH as compared with unstimulated controls (clear symbols).

FIG. 8 compares VCL and ALH in control (unstimulated clear symbols) and angiotensin II (AII) stimulated (solid symbols) sperm samples.

From the figures it is clear that angiotensin II amide stimulates both VCL and ALH, both parameters that are associated with increased fertility.

I claim:

1. A method of promoting in vitro fertilization of mammalian eggs comprising adding an effective amount of angiotensin II or a salt or amide analogue thereof to incubation medium containing oocytes and sperm, to promote fertilization.

2. The method of claim 1 wherein the effective amount of angiotensin II is added at a concentration of about 1 nmol/l.

3. The method of claim 1, wherein the amide analogue of angiotensin II is angiotensin II amide.

4. A method of improving the percentage motility of human sperm, the method comprising:
   adding an effective amount of angiotensin II or a salt or amide analogue thereof to the human sperm.

5. The method of claim 4, wherein the effective amount of angiotensin II or salt or amide analogue thereof is added at a concentration of about 1 nmol/l.

6. The method of claim 4, wherein the amide analogue of angiotensin II is angiotensin II amide.

7. A method of improving in vitro fertilization of a subject in need thereof comprising:
   adding angiotensin II or a salt or amide analogue thereof in an effective amount to human sperm of the subject; and
   increasing the percentage motility of the human sperm thereby.

8. The method of claim 7, wherein the angiotensin II or salt or amide analogue thereof is added at a concentration of about 1 nmol/l.

9. The method of claim 7, wherein the amide analogue of angiotensin II is angiotensin II amide.

10. A method of improving in vitro fertilization in a subject in need thereof comprising:
    adding angiotensin II or a salt or amide analogue thereof in an effective amount to the subject's sperm; and
    increasing the curvilinear velocity of the subject's sperm thereby.

11. The method of claim 10, wherein the angiotensin II or salt or amide analogue thereof is added at a concentration of about 1 nmol/l.

12. The method of claim 10, wherein the amide analogue of angiotensin II is angiotensin II amide.

13. A method of improving in vitro fertilization comprising:
   adding an effective amount of angiotensin II or a salt or amide analogue thereof to human sperm; and
   increasing the amplitude of lateral head displacement of the human sperm thereby.

14. The method of claim 13, wherein the angiotensin II or salt or amide analogue thereof is added at a concentration of about 1 nmol/l.

15. The method of claim 13, wherein the amide analogue of angiotensin II is angiotensin II amide.

16. A method of improving more than one of the following characteristics selected from the group consisting of curvilinear velocity, amplitude of lateral head displacement and percentage motility of human sperm, the sperm being in need of improvement in the more than one characteristic the method comprising:
   adding angiotensin II or a salt or amide analogue thereof in an effective amount to the human sperm.

17. The method of claim 16, wherein the angiotensin II or salt or amide analogue thereof is added at a concentration of about 1 nmol/l.

18. The method of claim 16, wherein the amide analogue of angiotensin II is angiotensin II amide.

19. A method of improving in vitro fertilization comprising:
   adding angiotensin II or a salt or amide analogue thereof in an effective amount to human sperm; and
   increasing more than one of the following characteristics selected from the group consisting of curvilinear velocity, amplitude of lateral head displacement, and percentage motility of human sperm thereby.

20. The method of claim 19, wherein the angiotensin II or salt or amide analogue thereof is added at a concentration of about 1 nmol/l.

21. The method of claim 20, wherein the amide analogue of angiotensin II is angiotensin II amide.

\* \* \* \* \*